US00PP16788P2

(12) United States Plant Patent
ter Laak

(10) Patent No.: US PP16,788 P2
(45) Date of Patent: Jul. 11, 2006

(54) POINSETTIA PLANT NAMED 'TEMPTATION RED'

(50) Latin Name: *Euphorbia pulcherrima*
Varietal Denomination: Temptation Red

(75) Inventor: Wendela Antoinette ter Laak, Aalsmeer (NL)

(73) Assignee: Florema Young Plants B.V., Amstelveen (NL)

( * ) Notice: Subject to any disclaimer, the term of this patent is extended or adjusted under 35 U.S.C. 154(b) by 38 days.

(21) Appl. No.: 11/069,279

(22) Filed: Mar. 1, 2005

(51) Int. Cl.
*A01H 5/00* (2006.01)

(52) U.S. Cl. ..... Plt./307
(58) Field of Classification Search ..... Plt./307
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Poinsettia plant named 'Temptation Red', characterized by its compact, uniform and upright plant growth habit; freely branching habit with strong lateral branches; dark green-colored leaves; early flowering habit; dark velvety red-colored flower bracts; and excellent post-production longevity.

2 Drawing Sheets

Botanical designation: *Euphorbia pulcherrima* Willd.
Cultivar denomination: 'Temptation Red'.

BACKGROUND OF THE INVENTION

The present Invention relates to a new and distinct cultivar of Poinsettia plant, botanically known as *Euphorbia pulcherrima* Willd., and hereinafter referred to by the name 'Temptation Red'.

The new Poinsettia was discovered and selected by the Inventor in a controlled environment in Amstelveen, The Netherlands in September, 2003, as a naturally-occurring whole plant mutation of *Euphorbia pulcherrima* Willd. 'Pimpernel Red', not patented. The new Poinsetta was observed as a single plant in a group of flowering plants of the parent cultivar.

Asexual reproduction of the new Poinsettia by terminal cuttings propagated in a controlled environment in Amstelveen, The Netherlands, since September, 2003, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Temptation Red'. These characteristics in combination distinguish 'Temptation Red' as a new and distinct cultivar:

1. Compact, uniform and upright plant growth habit.
2. Freely branching habit with strong lateral branches.
3. Dark green-colored leaves.
4. Early flowering habit.
5. Dark velvety red-colored flower bracts.
6. Excellent post-production longevity.

Compared to plants of the parent, the cultivar Pimpernel Red, plants of the new Poinsettia flower about three to four days earlier and have darker red-colored flower bracts.

Plants of the new Poinsettia can be compared to plants of the cultivar Fisson, disclosed in U.S. Plant Pat. No. 9,365. In side-by-side comparisons conducted in Amstelveen, The Netherlands, plants of the new Poinsettia flowered about one week earlier than plants of the cultivar Fisson. In addition, plants of the new Poinsettia had darker red-colored flower bracts than plants of the cultivar Fisson.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of a typical flowering plant of 'Temptation Red' grown in a container.

The photograph on the second sheet is a close-up view of a typical inflorescence of 'Temptation Red'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Amstelveen, The Netherlands during the autumn and winter under commercial practice in a glass-covered greenhouse with day temperatures ranging from 18 to 21° C., night temperatures ranging from 16 to 18° C. and light levels about 2,300 foot-candles. Single plants were grown in 13-cm pots and pinched once. Plants were flowered under natural season short day/long night conditions. Plants were about 16 weeks old when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Temptation Red.

Parentage: Naturally-occurring whole plant mutation of *Euphorbia pulcherrima* Willd. 'Pimpernel Red', not patented.

Propagation:

*Type cutting.*—Terminal cuttings.

*Time to initiate roots.*—About two weeks at 21° C.

*Time to develop roots.*—About three weeks at 21° C.

*Root description.*—Thick, fibrous, freely-branching; color, 158B.

Plant description:

*Plant form.*—Inverted triangle; top of plant mounded.

*Growth habit.*—Upright, compact and uniform plant habit; vigorous.

*Plant height.*—About 29 to 32 cm.

*Plant diameter or spread.*—About 40 to 45 cm.

*Lateral branch description.*—Quantity: About five to six lateral branches develop after pinching. Length: About 25 cm. Diameter: About 7 mm. Internode length: About 2.5 cm. Strength: Strong. Texture: Smooth; glabrous. Color: 183A.

*Foliage description.*—Arrangement: Alternate, simple. Length: About 12 to 13 cm. Width: About 9 to 10 cm. Shape: Ovate; lobed. Apex: Acuminate to acute. Base: Acute. Margin: Entire with irregular lobing. Venation pattern: Pinnate. Texture, upper and lower surfaces: Glabrous, smooth. Color: Developing and fully expanded foliage, upper surface: 131A. Developing and fully expanded foliage, lower surface: 136B. Venation, upper surface: 183B. Venation, lower surface: 183C. Petiole: Length: About 6 to 7 cm. Diameter: About 2 to 3 mm. Texture, upper and lower surfaces: Smooth; glabrous. Color: 183A.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Early flowering habit; response time, about 6.5 to 7.5 weeks.

*Post-production longevity.*—Plants of the new Poinsettia maintain good substance and bract color for at least four weeks under interior conditions.

*Inflorescence size.*—Diameter: About 30 cm. Height (depth): About 3 cm.

*Flower bracts.*—Quantity per inflorescence: About 15 to 20. Length: About 13 to 14 cm. Width: About 8 cm. Shape: Ovate. Apex: Acuminate. Base: Obtuse. Margin: Entire with irregular lobing. Texture, upper and lower surfaces: Smooth, glabrous; velvety. Surface: Rugose. Venation pattern: Pinnate. Color: Developing bracts, upper and lower surfaces: 46A. Fully developed bracts, upper surface: 46A. Fully developed bracts, lower surface: 46B. Venation, upper and lower surfaces: Similar to lamina. Bract petiole: Length: About 2 cm. Diameter: About 2 mm. Texture, upper and lower surfaces: Smooth; glabrous. Color: Close to 46A.

*Cyathia.*—Quantity per corymb: About ten. Diameter of cyathia cluster: About 2 cm. Length: About 1 cm. Width: About 6 mm. Shape: Ovoid. Color: Close to 146B. Peduncle: Length: About 2 to 3 mm. Diameter: About 1 mm. Strength: Strong. Aspect: Mostly upright. Texture: Smooth; glabrous. Color: 146D. Stamens: Quantity per cyathium: About 50. Anther shape: Oblong. Anther length: About 2 mm. Anther color: 183A. Amount of pollen: Abundant. Pollen color: 12A. Pistils: Quantity per cyathium: One. Length: About 8 mm. Stigma color: 183A. Style length: About 2 mm. Style color: 146D. Ovary color: 146D. Nectaries: Quantity per cyathium: About one or two. Size: About 3 mm by 4 mm. Color: 21A.

Disease/pest resistance: Resistance to pathogens and pests common to Poinsettias has not been observed on plants grown under commercial conditions.

It is claimed:

1. A new and distinct cultivar of Poinsettia plant named 'Temptation Red', as illustrated and described.

* * * * *

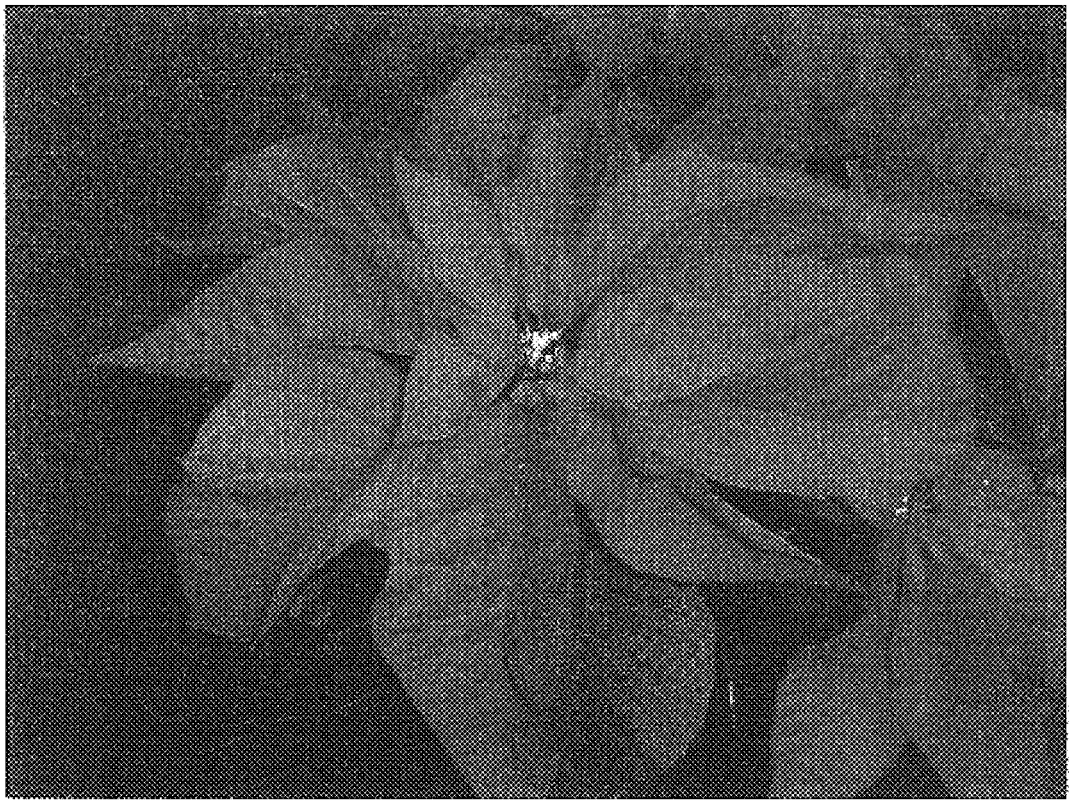

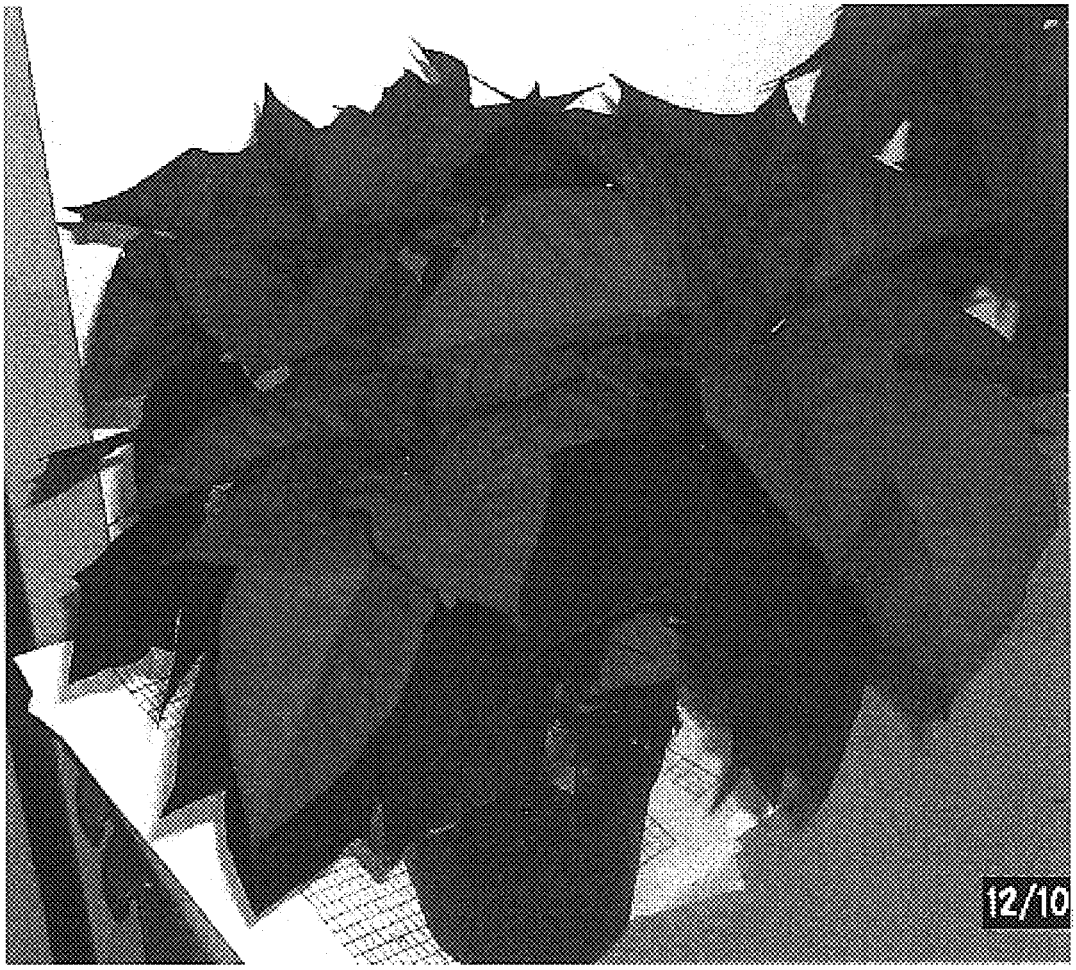
12/10